(12) United States Patent
Foerster et al.

(10) Patent No.: US 11,806,009 B2
(45) Date of Patent: **\*Nov. 7, 2023**

(54) DEVICE, SYSTEM, AND METHOD TO SECURE AN ARTICLE TO A TISSUE

(71) Applicant: VALCARE, INC., Newport Beach, CA (US)

(72) Inventors: Seth Foerster, San Clemente, CA (US); Nadav Yellin, Ramat Gan (IL); Samuel M. Shaolian, Newport Beach, CA (US); Jeffrey P. Dumontelle, Irvine, CA (US)

(73) Assignee: VALCARE, INC., Herzelyia Pituach (IL)

( * ) Notice: Subject to any disclaimer, the term of this patent is extended or adjusted under 35 U.S.C. 154(b) by 72 days.

This patent is subject to a terminal disclaimer.

(21) Appl. No.: 17/648,153

(22) Filed: Jan. 17, 2022

(65) Prior Publication Data
US 2022/0280153 A1  Sep. 8, 2022

Related U.S. Application Data (60) Continuation of application No. 16/196,223, filed on Nov. 20, 2018, now Pat. No. 11,224,422, which is a
(Continued)

(51) Int. Cl.
*A61B 17/064* (2006.01)
*A61B 17/068* (2006.01)
(Continued)

(52) U.S. Cl.
CPC ........ *A61B 17/0644* (2013.01); *A61B 17/068* (2013.01); *A61B 17/0684* (2013.01);
(Continued)

(58) Field of Classification Search
CPC .............. A61B 17/0644; A61B 17/068; A61B 17/0684; A61B 2017/00867;
(Continued)

(56) References Cited

U.S. PATENT DOCUMENTS

| 4,602,911 A | 7/1986 | Ahmadi et al. |
| 5,236,440 A | 8/1993 | Hlavacek et al. |

(Continued)

FOREIGN PATENT DOCUMENTS

| DE | 102014102653 A1 | 9/2015 |
| EP | 2600799 | 6/2013 |

(Continued)

OTHER PUBLICATIONS

12793292.9, Extended European Search Report, dated Dec. 1, 2014, 6 pages.
(Continued)

*Primary Examiner* — Brooke Labranche
(74) *Attorney, Agent, or Firm* — Dorsey & Whitney LLP (57) ABSTRACT

A device for securing an article to a tissue may include a body, transitionable from a deployment state to a securing state, having a first portion, a second portion, and a medial portion therebetween. The first portion and the second portion may each have an end configured to pierce the tissue. The device in the deployment state may have a linearly extended or a U-shaped structure. In the securing state, the first portion may be embedded in the tissue and the medial portion may contact the article. A system for securing the article to the tissue may releasably engage the device while in the deployment state. A method for securing the article may include contacting the article with a tissue surface and releasing the device from the system so that the device, in the securing state, may anchor the article to the tissue.

16 Claims, 8 Drawing Sheets

Related U.S. Application Data division of application No. 14/897,921, filed as application No. PCT/US2014/044920 on Jun. 30, 2014, now Pat. No. 11,058,417.

(60) Provisional application No. 61/840,588, filed on Jun. 28, 2013.

(51) Int. Cl.
    *A61B 17/00*     (2006.01)
    *A61B 17/04*     (2006.01)

(52) U.S. Cl.
    CPC .............. *A61B 2017/00867* (2013.01); *A61B 2017/0412* (2013.01); *A61B 2017/0645* (2013.01)

(58) Field of Classification Search
    CPC .... A61B 2017/0412; A61B 2017/0645; A61B 2017/0647
See application file for complete search history.

(56) References Cited

U.S. PATENT DOCUMENTS

| | | |
|---|---|---|
| 5,306,296 A | 4/1994 | Wright et al. |
| 5,695,518 A | 12/1997 | Laerum |
| 5,716,370 A | 2/1998 | Williamson, IV et al. |
| 5,855,614 A | 1/1999 | Stevens et al. |
| 6,113,611 A | 9/2000 | Allen et al. |
| 6,231,602 B1 | 5/2001 | Carpentier et al. |
| 6,447,524 B1 | 9/2002 | Knodel et al. |
| 6,619,291 B2 | 9/2003 | Hlavka et al. |
| 6,629,534 B1 | 10/2003 | St. Goar et al. |
| 6,669,687 B1 | 12/2003 | Saadat |
| 6,689,048 B2 | 2/2004 | Vanden Hoek et al. |
| 6,726,704 B1 | 4/2004 | Loshakove et al. |
| 6,776,784 B2 | 8/2004 | Ginn |
| 6,790,229 B1 | 9/2004 | Berreklouw |
| 6,797,002 B2 | 9/2004 | Spence et al. |
| 6,805,711 B2 | 10/2004 | Quijano et al. |
| 6,893,459 B1 | 5/2005 | Macoviak |
| 7,101,395 B2 | 9/2006 | Tremulis et al. |
| 7,114,953 B1 | 10/2006 | Wagner |
| 7,175,660 B2 | 2/2007 | Cartledge et al. |
| 7,238,191 B2 | 7/2007 | Bachmann |
| 7,285,087 B2 | 10/2007 | Moaddeb et al. |
| 7,297,150 B2 | 11/2007 | Cartledge et al. |
| 7,569,072 B2 | 8/2009 | Berg et al. |
| 7,594,887 B2 | 9/2009 | Moaddeb et al. |
| 7,635,329 B2 | 12/2009 | Goldfarb et al. |
| 7,655,040 B2 | 2/2010 | Douk et al. |
| 7,717,954 B2 | 5/2010 | Solem et al. |
| 7,722,668 B2 | 5/2010 | Moaddeb et al. |
| 7,758,637 B2 | 7/2010 | Starksen et al. |
| 7,837,729 B2 | 11/2010 | Gordon et al. |
| 7,988,725 B2 | 8/2011 | Gross et al. |
| 8,163,014 B2 | 4/2012 | Lane et al. |
| 8,182,529 B2 | 5/2012 | Gordon et al. |
| 8,236,049 B2 | 8/2012 | Rowe et al. |
| 8,287,591 B2 | 10/2012 | Keidar et al. |
| 8,518,107 B2 | 8/2013 | Tsukashima et al. |
| 8,579,968 B1 | 11/2013 | Shannon et al. |
| 11,058,417 B2 | 7/2021 | Foerster et al. |
| 11,191,536 B2 | 12/2021 | Foerster et al. |
| 11,224,422 B2 | 1/2022 | Foerster et al. |
| 2002/0151961 A1 | 10/2002 | Lashinski et al. |
| 2002/0151970 A1 | 10/2002 | Garrison et al. |
| 2002/0188170 A1 | 12/2002 | Santamore et al. |
| 2002/0198526 A1 | 12/2002 | Shaolian et al. |
| 2003/0050693 A1 | 3/2003 | Quijano et al. |
| 2003/0078465 A1 | 4/2003 | Pai |
| 2003/0078671 A1 | 4/2003 | Lesniak et al. |
| 2003/0191528 A1 | 10/2003 | Quijano et al. |
| 2003/0198605 A1 | 10/2003 | Montgomery et al. |
| 2003/0199974 A1 | 10/2003 | Lee et al. |
| 2004/0044364 A1 | 3/2004 | Devries et al. |
| 2004/0068276 A1 | 4/2004 | Golden et al. |
| 2004/0122514 A1 | 6/2004 | Fogarty et al. |
| 2004/0138744 A1 | 7/2004 | Lashinski et al. |
| 2004/0148021 A1 | 7/2004 | Cartledge et al. |
| 2004/0193191 A1 | 9/2004 | Starksen et al. |
| 2004/0243230 A1 | 12/2004 | Navia et al. |
| 2004/0249391 A1 | 12/2004 | Cummins |
| 2004/0260393 A1 | 12/2004 | Rahdert et al. |
| 2004/0260394 A1 | 12/2004 | Douk et al. |
| 2005/0020696 A1 | 1/2005 | Montgomery et al. |
| 2005/0033325 A1 | 2/2005 | May et al. |
| 2005/0065550 A1 | 3/2005 | Starksen et al. |
| 2005/0090846 A1 | 4/2005 | Pedersen et al. |
| 2005/0096740 A1 | 5/2005 | Langberg et al. |
| 2005/0113910 A1 | 5/2005 | Paniagua et al. |
| 2005/0137692 A1 | 6/2005 | Haug et al. |
| 2005/0137695 A1 | 6/2005 | Salahieh et al. |
| 2005/0203549 A1 | 9/2005 | Realyvasquez |
| 2005/0222678 A1 | 10/2005 | Lashinski et al. |
| 2005/0240200 A1 | 10/2005 | Berghaim |
| 2000/5028319 | 12/2005 | Hintema et al. |
| 2005/0267572 A1 | 12/2005 | Schoon et al. |
| 2005/0283190 A1 | 12/2005 | Huitema et al. |
| 2005/0288778 A1 | 12/2005 | Shaoulian et al. |
| 2005/0288781 A1 | 12/2005 | Moaddeb et al. |
| 2006/0009737 A1 | 1/2006 | Whiting et al. |
| 2006/0020327 A1 | 1/2006 | Lashinski et al. |
| 2006/0122633 A1 | 6/2006 | To et al. |
| 2006/0129025 A1 | 6/2006 | Levine et al. |
| 2006/0155165 A1 | 7/2006 | Vanden Hoek et al. |
| 2006/0161169 A1 | 7/2006 | Nieminen et al. |
| 2006/0184240 A1 | 8/2006 | Jimenez et al. |
| 2006/0184242 A1 | 8/2006 | Lichtenstein |
| 2006/0195134 A1 | 8/2006 | Crittenden et al. |
| 2006/0195183 A1 | 8/2006 | Navia et al. |
| 2006/0241748 A1 | 10/2006 | Lee et al. |
| 2006/0282161 A1 | 12/2006 | Huynh et al. |
| 2007/0016287 A1 | 1/2007 | Cartledge et al. |
| 2007/0027533 A1 | 2/2007 | Douk et al. |
| 2007/0038296 A1 | 2/2007 | Navia et al. |
| 2007/0051377 A1 | 3/2007 | Douk et al. |
| 2007/0067027 A1 | 3/2007 | Moaddeb et al. |
| 2007/0073098 A1 | 3/2007 | Lenker et al. |
| 2007/0080188 A1 | 4/2007 | Spence et al. |
| 2007/0093854 A1 | 4/2007 | Kayan |
| 2007/0118215 A1 | 5/2007 | Moaddeb |
| 2007/0128132 A1 | 6/2007 | Piergallini et al. |
| 2007/0135913 A1 | 6/2007 | Moaddeb et al. |
| 2007/0142907 A1 | 6/2007 | Moaddeb et al. |
| 2007/0213812 A1 | 9/2007 | Webler et al. |
| 2007/0233239 A1 | 10/2007 | Navia et al. |
| 2007/0239272 A1 | 10/2007 | Navia et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0250161 A1 | 10/2007 | Dolan |
| 2007/0293942 A1 | 12/2007 | Mirzaee |
| 2008/0177380 A1 | 7/2008 | Starksen et al. |
| 2008/0177381 A1 | 7/2008 | Navia et al. |
| 2008/0200980 A1 | 8/2008 | Robin et al. |
| 2008/0243220 A1 | 10/2008 | Barker |
| 2008/0262513 A1 | 10/2008 | Stahler et al. |
| 2008/0262609 A1 | 10/2008 | Gross et al. |
| 2008/0306586 A1 | 12/2008 | Cartledge et al. |
| 2009/0088838 A1 | 4/2009 | Shaolian et al. |
| 2009/0118747 A1 | 5/2009 | Bettuchi et al. |
| 2009/0125098 A1 | 5/2009 | Chuter |
| 2009/0149872 A1 | 6/2009 | Gross et al. |
| 2009/0216322 A1 | 8/2009 | Le et al. |
| 2009/0222083 A1 | 9/2009 | Nguyen et al. |
| 2009/0238778 A1 | 9/2009 | Mordas et al. |
| 2009/0299470 A1 | 12/2009 | Rao et al. |
| 2010/0010616 A1 | 1/2010 | Drews et al. |
| 2010/0030014 A1 | 2/2010 | Ferrazzi et al. |
| 2010/0063586 A1 | 3/2010 | Iasenkam et al. |
| 2010/0121433 A1 | 5/2010 | Bolling et al. |
| 2010/0161047 A1 | 6/2010 | Cabiri |

(56) References Cited

U.S. PATENT DOCUMENTS

| | | |
|---|---|---|
| 2010/0185274 A1 | 7/2010 | Moaddeb et al. |
| 2010/0211166 A1 | 8/2010 | Miller et al. |
| 2010/0249920 A1 | 9/2010 | Bolling |
| 2010/0266989 A1 | 10/2010 | Piergallini et al. |
| 2010/0280605 A1 | 11/2010 | Hammer et al. |
| 2010/0286767 A1 | 11/2010 | Zipory et al. |
| 2011/0022168 A1 | 1/2011 | Cartledge |
| 2011/0027753 A1 | 2/2011 | Maurat et al. |
| 2011/0034953 A1 | 2/2011 | Milo |
| 2011/0066231 A1 | 3/2011 | Cartledge et al. |
| 2011/0093062 A1 | 4/2011 | Cartledge et al. |
| 2011/0106245 A1 | 5/2011 | Miller et al. |
| 2011/0106247 A1 | 5/2011 | Miller et al. |
| 2011/0137397 A1 | 6/2011 | Chau et al. |
| 2011/0166649 A1 | 7/2011 | Gross et al. |
| 2011/0190879 A1 | 8/2011 | Bobo et al. |
| 2011/0208298 A1 | 8/2011 | Tuval et al. |
| 2011/0224785 A1 | 9/2011 | Hacohen |
| 2011/0257728 A1 | 10/2011 | Kuehn |
| 2011/0282361 A1 | 11/2011 | Miller et al. |
| 2011/0301698 A1 | 12/2011 | Miller et al. |
| 2011/0301699 A1 | 12/2011 | Saadat et al. |
| 2012/0022557 A1 | 1/2012 | Cabiri et al. |
| 2012/0022644 A1 | 1/2012 | Reich et al. |
| 2012/0059458 A1 | 3/2012 | Buchbinder et al. |
| 2012/0095455 A1 | 4/2012 | Rodmond et al. |
| 2012/0123531 A1 | 5/2012 | Tsukashima et al. |
| 2012/0136436 A1 | 5/2012 | Cabiri et al. |
| 2012/0165930 A1 | 6/2012 | Hanson et al. |
| 2012/0245604 A1 | 9/2012 | Tegzes |
| 2012/0310330 A1 | 12/2012 | Buchbinder et al. |
| 2013/0087598 A1 | 4/2013 | Surti |
| 2013/0116780 A1 | 5/2013 | Miller et al. |
| 2013/0166022 A1 | 6/2013 | Conklin |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0282114 A1 | 10/2013 | Schweich, Jr. et al. |
| 2013/0289718 A1 | 10/2013 | Tsukashima et al. |
| 2013/0289720 A1 | 10/2013 | Dobrilovic |
| 2013/0304197 A1 | 11/2013 | Buchbiner et al. |
| 2014/0005778 A1 | 1/2014 | Buchbinder et al. |
| 2014/0046433 A1 | 2/2014 | Kovalsky |
| 2014/0058505 A1 | 2/2014 | Bielefeld |
| 2014/0114407 A1 | 4/2014 | Rajamannan |
| 2015/0173897 A1 | 6/2015 | Raanani et al. |
| 2015/0173987 A1 | 6/2015 | Albinmousa et al. |
| 2015/0351903 A1 | 12/2015 | Morriss et al. |
| 2016/0022419 A1 | 1/2016 | Yellin et al. |
| 2016/0038286 A1 | 2/2016 | Yellin et al. |
| 2016/0089235 A1 | 3/2016 | Yellin |
| 2016/0106420 A1 | 4/2016 | Foerster et al. |
| 2016/0120642 A1 | 5/2016 | Shaolian et al. |
| 2016/0120645 A1 | 5/2016 | Alon |
| 2017/0042670 A1 | 2/2017 | Shaolian et al. |
| 2017/0231763 A1 | 8/2017 | Yellin |
| 2018/0042723 A1 | 2/2018 | Yellin et al. |
| 2019/0083091 A1 | 3/2019 | Foerster |
| 2019/0083092 A1 | 3/2019 | Foerster et al. |

FOREIGN PATENT DOCUMENTS

| | | |
|---|---|---|
| EP | 2967700 A1 | 1/2016 |
| KR | 1020040095482 A | 11/2004 |
| RU | 125062 U1 | 2/2013 |
| WO | 199009153 A1 | 2/1990 |
| WO | 2003017874 A1 | 3/2003 |
| WO | 2003047467 A1 | 6/2003 |
| WO | 2005046488 A2 | 5/2005 |
| WO | 2009052427 A1 | 4/2009 |
| WO | 2009120764 A2 | 10/2009 |
| WO | 2010004546 A1 | 1/2010 |
| WO | 2010085659 A1 | 7/2010 |
| WO | 2011011443 A1 | 1/2011 |
| WO | 2011097355 A2 | 8/2011 |
| WO | 2012004679 A2 | 1/2012 |
| WO | 2012019052 A1 | 2/2012 |
| WO | 2012063228 A1 | 5/2012 |
| WO | 2012095159 A2 | 6/2012 |
| WO | 2012167095 A2 | 12/2012 |
| WO | 2013095816 A1 | 6/2013 |
| WO | 2013128436 A1 | 9/2013 |
| WO | 2013130641 A1 | 9/2013 |
| WO | 2013175468 A2 | 11/2013 |
| WO | 2014145399 A1 | 9/2014 |
| WO | 2014178869 A1 | 11/2014 |
| WO | 2014189509 A1 | 11/2014 |
| WO | 2014190329 A1 | 11/2014 |
| WO | 2014210600 A1 | 12/2014 |
| WO | 2014210600 A2 | 12/2014 |
| WO | 2015132668 A1 | 9/2015 |
| WO | 2018035118 A1 | 2/2018 |

OTHER PUBLICATIONS 13755441.6, Partial European Search Report, dated Nov. 3, 2015, 7 pages.
U.S. Appl. No. 14/897,921, Notice of Allowance, dated Mar. 18, 2021, 9 pages.
14762806.9, Extended European Search Report, dated Jul. 29, 2016, 7 pages.
14817662.1, Extended European Search Report, dated Jan. 23, 2017, 7 pages.
U.S. Appl. No. 16/196,444, Non-Final Office Action, dated Jan. 19, 2021, 10 pages.
17155803.4, Extended European Search Report, dated Aug. 9, 2017, 7 pages.
Lendlein , et al., "Biodegradable, Elastic Shape-Memory Polymers for Potential Biomedical Applications", Science, vol. 296, May 31, 2002, pp. 1673-1676.
PCT/US2011/046659, International Search Report and Written Opinion, dated Jun. 4, 2012, 13 pages.
PCT/US2019/064289 , International Search Report and Written Opinion, dated Feb. 5, 2020.
PCT/US2012/040481 , International Search Report and Written Opinion, dated Dec. 6, 2012, 12 pages.
PCT/US2013/028065 , International Search Report and Written Opinion, dated Jun. 27, 2013, 12 pages.
PCT/US2013/042275 , International Search Report and Written Opinion, dated Feb. 20, 2014, 18 pages.
PCT/US2013/042275 , International Search Report and Written Opinion, dated Nov. 24, 2015, 18 pages.
PCT/US2013/058102 , International Search Report and Written Opinion, dated Apr. 21, 2014.
PCT/US2013/073552 , International Search Report and Written Opinion, dated Mar. 6, 2014, 4 pages.
PCT/US2014/030163 , International Search Report and Written Opinion, dated Aug. 27, 2014, 12 pages.
PCT/US2014/039454 , International Search Report and Written Opinion, dated Oct. 22, 2014, 10 pages.
PCT/US2014/039545 , International Search Report and Written Opinion, dated Oct. 22, 2014.
PCT/US2014/044920 , International Search Report and Written Opinion, dated Dec. 24, 2014, 14 pages.
14801009.3, Examination Report, dated Sep. 27, 2018.
PCT/US2017/046933 , International Search Report and Written Opinion, dated Dec. 21, 2017, 10 pages.
PCT/US2018/022910 , International Search Report and Written Opinion, dated May 23, 2018, 6 pages.

DEVICE, SYSTEM, AND METHOD TO SECURE AN ARTICLE TO A TISSUE

CLAIM OF PRIORITY

This application is a continuation of U.S. application Ser. No. 16/196,223, entitled "DEVICE, SYSTEM, AND METHOD TO SECURE AN ARTICLE TO A TISSUE," filed Nov. 20, 2018, which is a divisional of U.S. application Ser. No. 14/897,921, entitled "DEVICE, SYSTEM, AND METHOD TO SECURE AN ARTICLE TO A TISSUE," filed Dec. 11, 2015, which is a U.S. national stage filing under 35 U.S.C. § 371 of International Application No. PCT/US2014/044920 entitled "DEVICE, SYSTEM, AND METHOD TO SECURE AN ARTICLE TO A TISSUE," filed Jun. 30, 2014, which claims benefit of and priority to U.S. Provisional Patent Application No. 61/840,588, entitled "STAPLE AND METHOD TO DELIVER IT TO A TARGET SITE," filed Jun. 28, 2013, the disclosures of which are incorporated herein by reference in their entirety.

BACKGROUND

Staples exist for a variety of applications in the medical field. There are staples that may fix soft tissues, boney tissues, and soft tissues to boney tissues. Some staples may bring two or more tissues together while the staples are applied. Alternatively, staples may function to fix together some tissues that are brought together by other means, such as by mechanical or chemical means (shape memory).

In some applications, staples may be designed to bring tissues together so the tissues may heal. In some alternative applications, one or more staples may be used to hold or otherwise affix an instrument or other structure to one or more tissues. In some instances, however, an instrument or structure may not be adapted to work with a staple due to size or geometry.

Such medical staples may find use in a number of surgical or non-surgical procedures including, without limitation, an open surgical procedure, an arthroscopic procedure, or in less invasive procedures. Additionally, staples may include additional features suited to specialty applications including imaging applications, such as radiographic procedures.

SUMMARY

In an embodiment, a device for securing an article to a tissue may be composed of a body, transitionable from a first deployment state to a second securing state, having a first portion, a second portion, and a medial portion between the first portion and the second portion, in which the first portion has a first terminal end configured to pierce the tissue, and in which the second securing state comprises at least a section of the first portion of the body assuming a curved geometry embedded in the tissue and at least a section of the medial portion of the body contacting a surface of the article.

In an embodiment, a device for securing an article to a tissue may be composed of a body, transitionable from a first deployment state to a second securing state, having a first portion, a second portion, and a medial portion between the first portion and the second portion, in which the first portion has a first terminal end configured to pierce the tissue, and a tab standoff in mechanical communication with the medial portion of the body at a first end and a tab at a second end, in which the tab is displaced by a slot from the body. The first deployment state of the device may be a linearly extended state. In the second securing state, the device has at least a section of the first portion of the body assuming a curved geometry embedded in the tissue and at least a section of the second portion contacting a surface of the article.

In an embodiment, a device for securing an article to a tissue may be compose of a body, transitionable from a first deployment state to a second securing state, having a first portion, a second portion, and a medial portion between the first portion and the second portion, in which the first portion has a first terminal end configured to pierce the tissue and the second portion has a second terminal end configured to pierce the tissue. The first deployment state may be a U-shaped state. In the second securing state, the device has at least a section of the first terminal end assuming a curved geometry embedded in the tissue, at least a section of the second terminal end assuming a curved geometry embedded in the tissue, and at least a section of the medial portion contacting a surface of the article.

In an embodiment, system for securing an article to a tissue by releasibly engaging at least one securing device may be composed of an exterior tube having a distal end, in which at least a portion of the distal end of the exterior tube is configured to form a stable mechanical contact between the article and the tissue, and a push rod at least partially disposed within the interior tube. The system may be configured to releasibly engage at least one securing device having a body transitionable from a first deployment state to a second securing state, and the push rod may be configured to effect a release of the at least one securing device, thereby allowing the securing device body to transition from the first deployment state to the second securing state.

In an embodiment, a method of securing an article to a tissue, may be composed of providing a system for securing the article to the tissue, the system composed of a housing having a distal end, in which at least a portion of the distal end of the housing is configured to engage the article with a surface of the tissue, providing at least one securing device composed of a body, transitionable from a first deployment state to a second securing state, having a first portion, a second portion, and a medial portion between the first portion and the second portion, in which the first portion has a first terminal end configured to pierce the tissue, and wherein the second securing state comprises at least a section of the first portion of the body assuming a curved geometry embedded in the tissue and at least a section of the medial portion of the body assuming a curved geometry around a surface of the article, releasibly engaging the securing device in the first deployment state within the system for securing the article, engaging, by least a portion of the distal end of the housing, the article with the surface of the tissue, releasing the securing device from the distal end of the housing, thereby allowing the body to assume the second securing state and securing the article against the surface of the tissue.

DETAILED DESCRIPTION

In some applications, there may be a need to attach an article to a tissue, and especially a need for the article to be in close proximity to (for example, in physical contact with) the tissue. In many surgical procedures, articles may be secured through the use of one or more sutures, staples, and clamps. Sutures may be used in a wide variety of procedures because sutures, comprising flexible material, may take on the shape of the surface of the article being attached. However, suturing is a time-consuming process, and there may be variability in the degree of stabilization of the article to the tissue surface due to the innate variability of suture application. Additionally, the flexible suturing material may have a limited tensile strength that may not be strong enough for some applications.

Staples and clips may require less time to apply. Staplers, used to apply the staples, may provide more consistent force for securing the article to the tissue. As a result, there is less variability in force applied to the article, especially if a number of staples are used. Such staples and clips are typically made of metal, which has a greater tensile strength than sutures. However, staples and clips, because they are more rigid than sutures, may not readily conform to the surface of the article being secured. As a result, the article secured by the staples or clips may shift because the clip/article interface is not exact.

Disclosed herein is a device for securing an article to a tissue in which the device combines useful features of both sutures and staples. Specifically, the securing device disclosed herein may adjust to the surface geometry of the article being secured while being easily applied from a stapler-type system. In some examples, the article may include one or more cardiovascular implant articles. In some examples, the tissue may comprise a soft tissue such as one or more of a muscle tissue, a tendon tissue, a ligament tissue, and a cardiovascular tissue.

In some applications, the device may place the article in close proximity to the tissue. Alternatively, the device may be used to cause the article to physically contact the tissue. In some alternative applications, the securing device may be used to secure two portions of tissue together with or without securing a non-tissue article thereto.

Additionally, a system for deploying the device is disclosed herein. In some embodiments, the system may be an arthroscopic delivery device or may be part of an arthroscopic device. Such arthroscopic devices may be used, for example, during open surgical procedures or in minimally invasive surgical procedures. In some medical procedures, it may be necessary to visualize the attachment of the device to the tissue and article. Examples of visualization methods may include radiographic methods and ultrasound methods. The device disclosed herein generally has a two dimensional design and function, thereby accommodating such visualization techniques.

The disclosed device can be used in a variety of procedures in which one or more devices and/or one or more tissues may be involved. In one example, an article may be partially pre-attached to a tissue by an alternative means, such as by gluing, and a more robust attachment is required. In another example, the article may be in physical proximity to the tissue but may lack any secure attachment. In yet another example, the article may be completely attached to the tissue and additional locking between the article and the tissue may be required.

In one non-limiting example, the article may include one or more sutures or polymers and the tissue may include one of the papillary muscles. Such a procedure may find use in repairing or replacing one or more of the chordae tendineae by providing an anchor for the suture or polymer in the muscle to which the replacement may be attached.

The disclosed device can also be used as a means to attach two articles together. In one non-limiting embodiment, the first article may be a previously implanted article already fixed at a target site and the second article may be a new structure to be fixed to the first article and/or the surrounding tissue. As a non-limiting example, the first article may be a D-shaped or round annuloplasty ring that is implanted in a mitral valve annulus, and the second article may include a prosthetic valve designed to work in concert with the annuloplasty ring.

As disclosed herein, the securing device may take on a variety of embodiments as depicted in FIGS. 1A-1C and 2A-2F. It may be understood that such figures and embodiments are only examples and are not limiting. Common to all the possible embodiments of the securing device is the ability of the device to transition between a deployment state and a securing state. The deployment state may comprise a geometry consistent with a device adapted to deliver the securing device, and may include, without limitation, a linearly extended geometry or a U-shaped geometry. The securing state may comprise a geometry capable of contacting the article with a tissue or other article and securing the article thereto. In some non-limiting embodiments, the securing state may include contacting a portion of the securing device with at least a portion of a surface of the article to be secured, and embedding at least one terminal or end portion of the securing device in the tissue. The at least one terminal or end portion of the securing device, in the securing state, may include a curved or angled geometry within the tissue, thereby providing an anchor for the device. It may be understood that the device, in transitioning from the deployment state to the securing state may assume any appropriate intermediate geometry consistent with the initial (deployment) and final (securing) states.

Such securing devices may derive their property of transitioning from a first geometric state to a second geometric state from the material or materials from which they are made. In particular, the securing devices disclosed herein may comprise one or more materials having a high yield stress and high level of recoverable plastic strain. As a result of these properties, the device may be deformed from its relaxed shape (comprising the securing state) into a second shape (the deployment state) under force, but will return to the original relaxed shape once the force is removed.

In some non-limiting examples, the body of the securing device may include one or more of a metal, a polymer, and a plastic. Non-limiting examples of such metals may include 316 stainless steel, a cobalt chromium alloy, and combinations and alloys thereof. In some non-limiting examples, the body of the securing device may include one or more of a biocompatible material and a bio-absorbable material. In some non-limiting examples, the biocompatible material may include polyether ether ketone, a polyetherimide, or similar material. In some non-limiting examples, the body of the securing device may include one or more of a superelastic material and a shape memory alloy. A non-limiting example of such a shape memory alloy may include a nickel titanium alloy.

In addition to the materials to provide appropriate material properties, the securing devices may also include materials specific for the securing device function or use. Thus, in some embodiments, at least a portion of the body of the securing device may include a material that is visualizable by a radiological technique, an MRI technique, and an ultrasound technique.

In general, there are no limitations to any one or more of the physical dimensions of the securing device, as the dimensions of any one securing device may depend, at least in part, on the article to be secured, the tissue to which it may be secured, and the system used to deploy the securing device and secure the article. In one embodiment, the body of the securing device may have a length of about 10 mm to about 30 mm. Examples of the body length of the securing device may include a length of about 10 mm, about 12 mm, about 14 mm, about 16 mm, about 18 mm, about 20 mm, about 22 mm, about 24 mm, about 26 mm, about 28 mm, about 30 mm, and any value or range between any two of these values including endpoints. In one non-limiting example, the body of the securing device may have a length of about 20 mm. In some securing devices, the body may have a cross-sectional diameter of about 0.2 mm to about 1 mm. Examples of the body cross-sectional diameter of the securing device may include a diameter of about 0.2 mm, about 0.3 mm, about 0.4 mm, about 0.5 mm, about 0.6 mm, about 0.7 mm, about 0.8 mm, about 0.9 mm, about 1 mm, and any value or range between any two of these values including endpoints. In one non-limiting example, the body of the securing device may have a cross-sectional diameter of about 0.5 mm.

In some embodiments, at least a portion of the body of the securing device may have a circular cross-section. In some securing devices, the body may have a circular cross-sectional diameter of about 0.2 mm to about 1.5 mm. Examples of the circular cross-sectional diameter of the securing device may include a diameter of about 0.2 mm, about 0.3 mm, about 0.4 mm, about 0.5 mm, about 0.6 mm, about 0.7 mm, about 0.8 mm, about 0.9 mm, about 1 mm, about 1.3 mm, about 1.5 mm, and any value or range between any two of these values including endpoints. In one non-limiting example, the body of the securing device may have a circular cross-sectional diameter of about of about 0.8 mm.

In some embodiments, at least a portion of the body of the securing device may have a square or rectangular cross section. In some securing devices, the body may have a rectangular cross-section having a first cross-sectional diameter of about 0.2 mm to about 1 mm and a second cross-sectional diameter of about 0.2 mm to about 1 mm. Examples of the first cross-sectional diameter of the securing device may include a diameter of about 0.2 mm, about 0.3 mm, about 0.4 mm, about 0.5 mm, about 0.6 mm, about 0.7 mm, about 0.8 mm, about 0.9 mm, about 1 mm, and any value or range between any two of these values including endpoints. Examples of the second cross-sectional diameter of the securing device may include a diameter of about 0.2 mm, about 0.3 mm, about 0.4 mm, about 0.5 mm, about 0.6 mm, about 0.7 mm, about 0.8 mm, about 0.9 mm, about 1 mm, and any value or range between any two of these values including endpoints. In one non-limiting example, a securing device having a rectangular cross-section may have a first cross-sectional diameter of about 0.5 mm and a second cross-sectional diameter of about 0.8 mm.

Figure 1A:
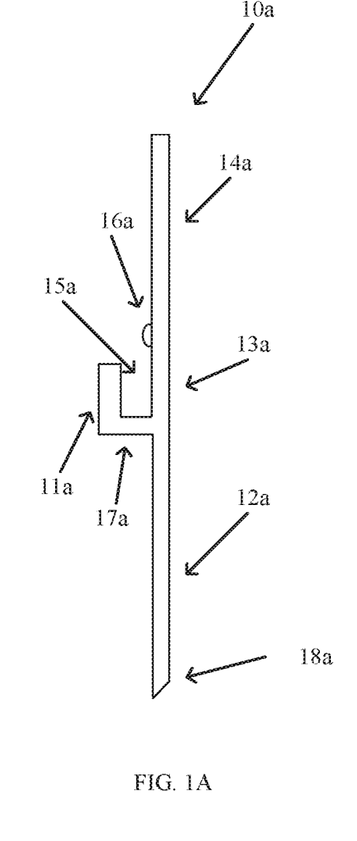
FIG. 1A depicts a side view of a securing device having a linearly extended deployment state according to an embodiment.
Figure 1B:
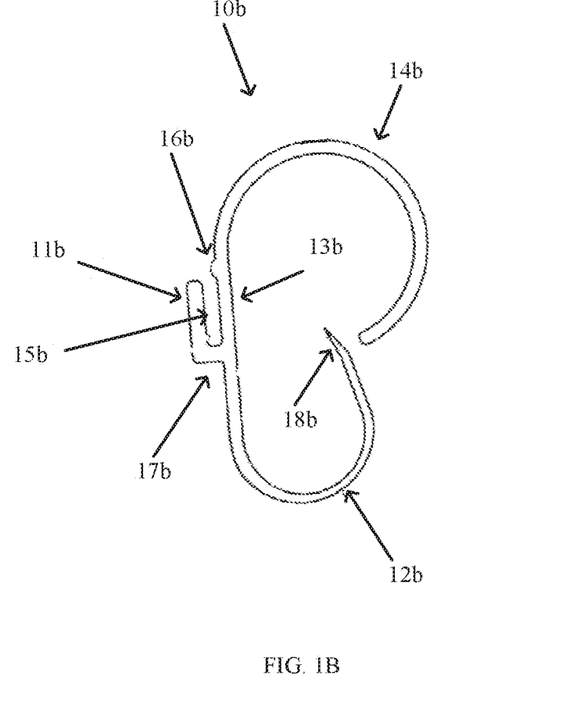
FIG. 1B depicts a side view of a securing state of a securing device having a linearly extended deployment state according to an embodiment.

FIG. 1A depicts a side view of one embodiment of a securing device having a linearly extended deployment state. FIG. 1B depicts a side view of the same securing device as FIG. 1A in the securing state.

As depicted in FIG. 1A, the securing device in the deployment state 10a may include a first portion 12a, a second portion 14a, and a medial portion 13a between the first portion and the second portion. The first portion 12a, the second portion 14a, and the medial portion 13a together may all form a linearly extended structure. The first portion 12a may have a first terminal end 18a having a sharpened point for penetrating the tissue. In some alternative embodiments, the first terminal end 18a may include one or more barbs, one or more serrations, one or more hooks, or any combination thereof. The second portion 14a may have a second terminal end (not shown) which, in some embodiments, may be a blunt end. The securing device in the deployment state 10a may also include a tab standoff 17a that is connected to a tab 11a on one end and to the medial portion 13a of the securing device on the other end. The tab 11a may be displaced from the medial portion 13a by a slot 15a.

In some non-limiting examples, the tab 11a may have a length of about 2 mm to about 7 mm. Examples of the length of the tab 11a may include a length of about 2 mm, about 3 mm, about 4 mm, about 5 mm, about 6 mm, about 7 mm, and any value or range between any two of these values including endpoints. In one non-limiting example, the tab 11a may have a length of about 5 mm. In some non-limiting examples, the tab 11a may have a width of about 0.2 mm to about 1 mm. Examples of the width of the tab 11a may include a width of about 0.2 mm, about 0.3 mm, about 0.4 mm, about 0.5 mm, about 0.6 mm, about 0.7 mm, about 0.8 mm, about 0.9 mm, about 1 mm, and any value or range between any two of these values including endpoints. In one non-limiting example, the tab 11a may have a width of about 0.5 mm. In some non-limiting examples, the tab 11a may be displaced from the medial portion 13a of the body of the securing device by a slot 15a having by a distance of about 0.5 mm to about 3 mm from the medial portion. Examples of the distance of the tab 11a from the medial portion 13a of the body may include a distance of about 0.5 mm, about 1 mm, about 1.5 mm, about 2 mm, about 2.5 mm, about 3 mm, and any value or range between any two of these values including endpoints. In one non-limiting example, the tab 11a may have distance from the medial portion 13a of the body of about 1.5 mm.

The securing device in the deployment state 10a may also include a friction protrusion 16a in mechanical communication with the medial portion of the body 13a and proximate to the tab 11a. In some embodiments, the tab 11a may have a first end in mechanical communication with the tab standoff 17a and have a second free end approximately opposite the friction protrusion 16a without making physical contact with it. In some alternative embodiments, the second free end of the tab 11a may be in mechanical contact with the friction protrusion 16a. The friction protrusion 16a and the tab 11a may help secure the securing device in the extended state 10a to a system configured to deploy it, as disclosed below.

In some non-limiting embodiments, the friction protrusion 16a may have a height of about 0.2 mm to about 1 mm. Examples of the height of the friction protrusion 16a may include a height of about 0.2 mm, about 0.3 mm, about 0.4 mm, about 0.5 mm, about 0.6 mm, about 0.7 mm, about 0.8 mm, about 0.9 mm, about 1 mm, and ranges between any two of these values including endpoints. In one non-limiting example, the friction protrusion 16a may have a height of about 0.5 mm.

As depicted in FIG. 1B, the securing device in FIG. 1A may assume a securing state 10b including a first portion 12b, a second portion 14b, and a medial portion 13b between the first portion and the second portion. In contrast to FIG. 1A, the first portion 12b in FIG. 1B may assume a curved geometry. The first terminal end 18b of the first portion 12b may include a sharpened point that may help anchor the securing device in the securing state 10b to the tissue. In some alternative embodiments, the first terminal end 18b may include one or more barbs, one or more serrations, one or more hooks, or any combination thereof. Also in contrast to FIG. TA, the second portion 14b in FIG. 1B may assume a curved geometry. The securing device in the securing state 10b may also include a tab standoff 17b that is connected to a tab 11b on one end and to the medial portion 13b of the securing device on the other end. The tab 11b may be displaced from the medial portion 13b by a slot 15b.

Figure 1C:
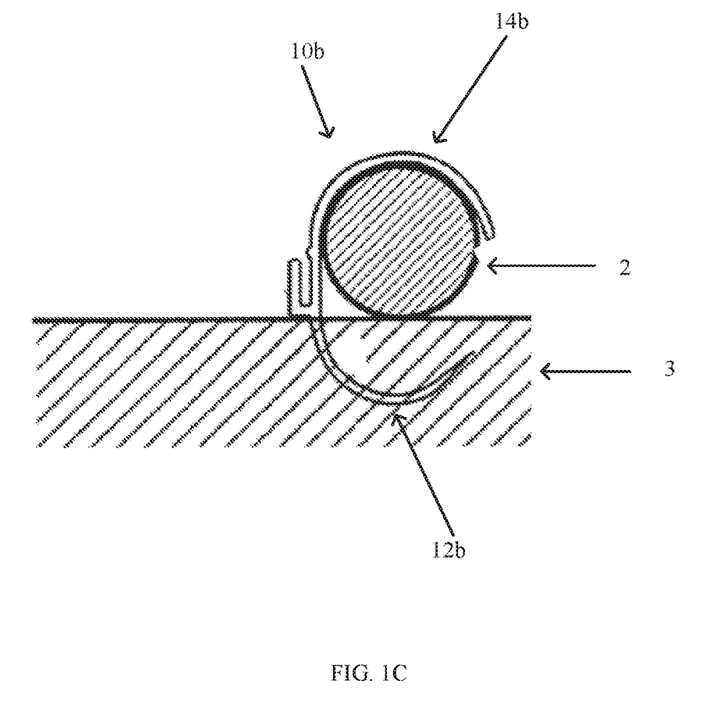
FIG. 1C depicts a side view of an article secured to a tissue surface by a securing device having a linearly extended deployment state according to an embodiment.

FIG. 1C depicts a manner in which an article may be secured to the surface of a tissue by the securing device depicted in FIGS. 1A and 1B. As illustrated in FIG. 1C, the article 2 may be held against the surface of a tissue 3 by means of the securing device in the securing state 10b. The first portion 12b of the device may assume a curved geometry within the tissue 3, thereby forming a tissue anchor for the device. The second portion 14b of the device may contact at least a portion of a surface of the article 2, thereby securing the article against the surface of the tissue 3. The medial portion of the device may also be in contact with at least a portion of the surface of the article 2. In some non-limiting embodiments, the second portion 14b may form a curved geometry around the surface of the article 2.

Figure 2A:
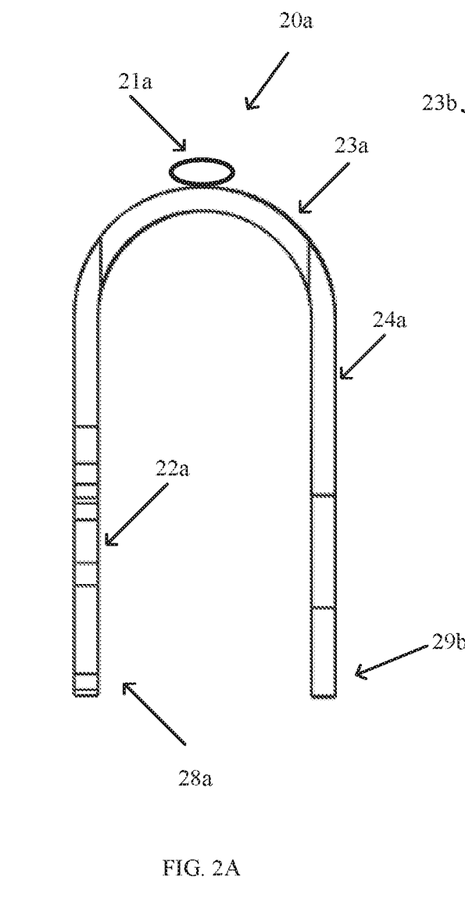
FIG. 2A depicts a side view of a securing device having a U-shaped deployment state according to an embodiment.
Figure 2B:
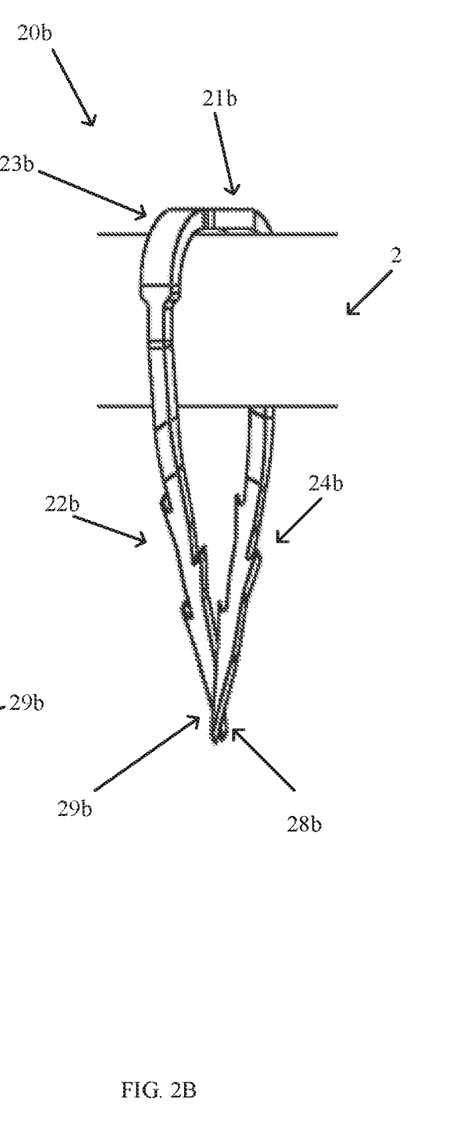
FIG. 2B depicts a 3-D view of an article secured by a securing device having a U-shaped deployment state according to an embodiment.

FIG. 2A depicts a side view of another embodiment of a securing device having a U-shaped deployment state. FIG. 2B depicts a side view of the same securing device as FIG. 2A in the securing state.

As depicted in FIG. 2A, the securing device in the deployment state 20a may include a first portion 22a, a second portion 24a, and a medial portion 23a between the first portion and the second portion. In contrast to the securing device depicted in FIG. 1A, the first portion 22a and the second portion 24a in the deployment state 20a do not form a linearly extended structure, but may be effectively parallel to each other. If the medial portion 23a is curved, the deployment state 20a may form a U-shaped structure. The first portion 22a may have a first terminal end 28a having a sharpened point for penetrating the tissue. In some alternative embodiments, the first terminal end 28a may include one or more barbs, one or more serrations, one or more hooks, or any combination thereof. The second portion 24a may have a second terminal end 29a which may have a sharpened point for penetrating the tissue. In some alternative embodiments, the second terminal end 29a may include one or more barbs, one or more serrations, one or more hooks, or any combination thereof. The securing device in the deployment state 20a may also include additional features 21a connected to the medial portion 23a of the securing device. The additional features 21a may be used to secure the device in the deployment state 20a within a system to secure an article to a surface of a tissue through the use of one or more securing devices. The additional features 21a may include a thickened section of the medial portion 23a, a broadened section of the medial portion, a flanged section of the medial portion, a perforated section of the medial portion, a hooked section of the medial portion (as depicted, for example, in FIG. 2E), or any combination thereof.

As depicted in FIG. 2B, the securing device in FIG. 2A may assume a securing state 20b including a first portion 22b, a second portion 24b, and a medial portion 23b between the first portion and the second portion. In contrast to FIG. 2A, the first portion 22b in FIG. 2B may assume a curved geometry within the tissue. The first terminal end 28b of the first portion 22b may include a sharpened point that may help anchor the securing device in the securing state 20b to the tissue. In some alternative embodiments, the first terminal end 28b may include one or more barbs, one or more serrations, one or more hooks, or any combination thereof. Also in contrast to FIG. 2A, the second portion 24b in FIG. 2B may assume a curved geometry while embedded in the tissue. The second terminal end 29b of the second portion 24b may include a sharpened point that may help anchor the securing device in the securing state 20b to the tissue. In some alternative embodiments, the second terminal end 29b may include one or more barbs, one or more serrations, one or more hooks, or any combination thereof. As depicted in FIG. 2B, the article 2 to be secured to the tissue may be contacted by a section of the first portion 22b, a section of the medial portion 23b, and a section of the second portion 24b. The additional features 21b may also be configured to assist with stabilizing the article 2 within the securing device in the securing state 20b.

Figure 2C:
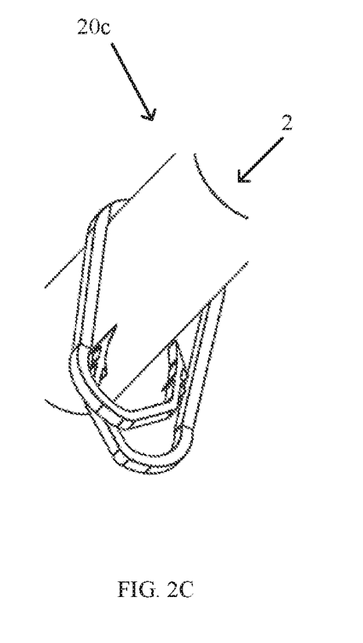
FIGS. 2C-2F depict 3-D views of exemplary securing states attainable by a securing device having a U-shaped deployment state according to an embodiment.
Figure 2D:
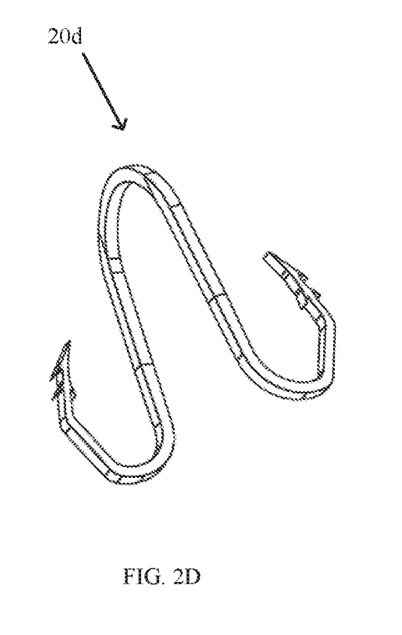
Figure 2E:
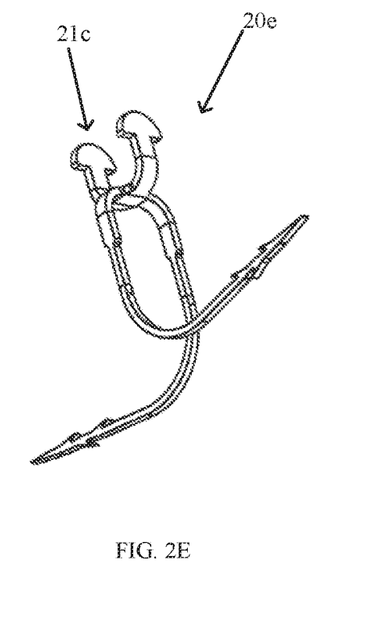
Figure 2F:
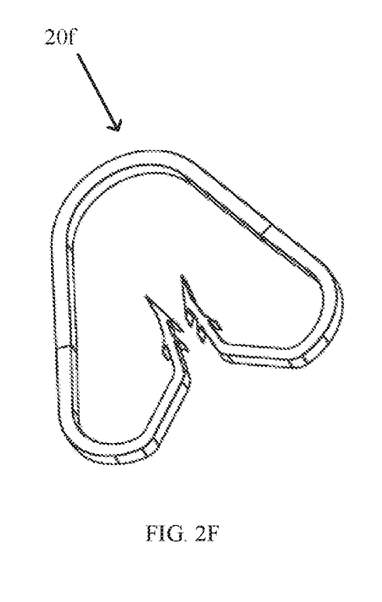

It may be appreciated that securing devices having parallel first and second portions in the deployment state may assume any of a number of different geometries in the securing state. For example, as depicted in FIG. 2B, the securing state may include the first and second portions or the first and second terminal ends forming a scissor-like geometry within the tissue, thereby holding the article between them. As depicted in FIG. 2C, the first and second portions or the first and second terminal ends may form a pair of opposing fish-hooks in the tissue and below the article. As depicted in FIG. 2D, the first and second portions or the first and second terminal ends may form a pair of opposing fish-hooks in the tissue that point away from the article. As depicted in FIG. 2E, the first and second portions or the first and second terminal ends may form a pair of opposing barbs in the tissue that point away from the article. As depicted in FIG. 2F, the first and second portions or the first and second terminal ends may form a clothes-pin-type arrangement within the tissue pointing towards the article. It may be understood that the specific geometric arrangements of the first portion, first terminal end, second portion, and second terminal end in the securing state as depicted in FIGS. 2B-2F are merely representative examples, and do not limit the possible configurations achievable by the securing device.

Figure 3A:
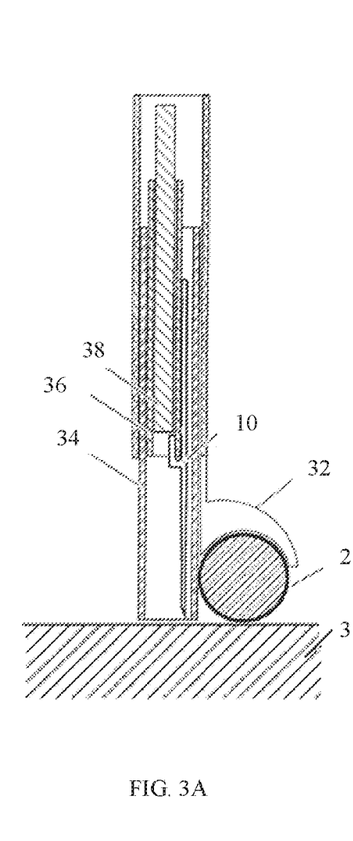
FIGS. 3A-3C depict use of a system to secure an article to a surface of a tissue using a securing device having a linearly extended deployment state according to an embodiment.
Figure 3B:
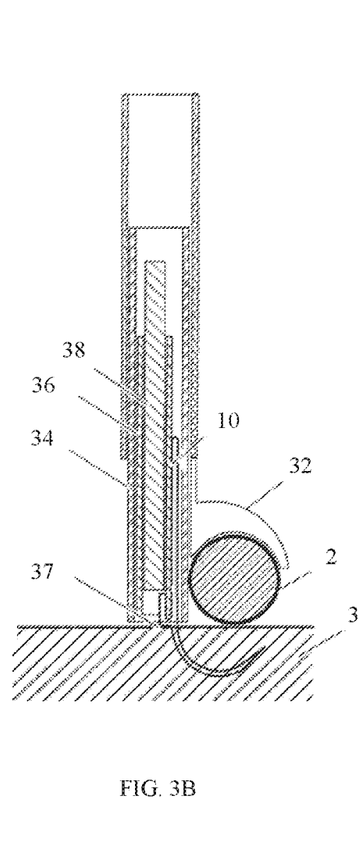
Figure 3C:
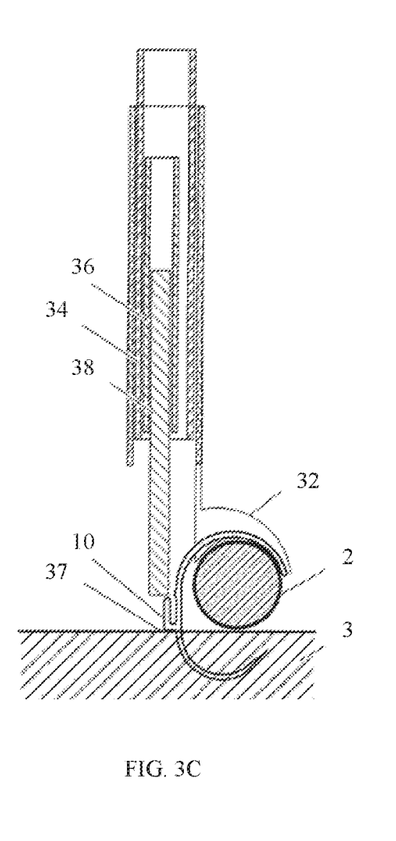

FIGS. 3A-3C depict one type of system configured to deploy a securing device and secure an article therewith to a surface of a tissue. The system may be used with a securing device having a linearly extended deployment state.

The system may include an exterior tube 31 that may house the remaining components. In one embodiment, the exterior tube 31 may include, at a distal end, a portion configured to form a mechanically stable contact between the article 2 and the surface of the tissue 3. In one non-limiting example, the portion of the exterior tube 31 may comprise a pawl 32. The pawl 32 may have a surface geometry complementary to the geometry of at least a portion of an external surface of the article 2. The exterior tube 31 may be composed of one or more of a metal and a plastic. In some embodiments, the exterior tube 31 may be composed of one or more of a stainless steel, a nickel titanium alloy, and a cobalt chrome alloy. In some embodiments, the exterior tube 31 may be composed of one or more of a polyether ether ketone, a polyether block amide, a polytetrafluoroethylene, a fluorinated ethylene propylene, and an extended polytetrafluoroethylene.

In general, there are no limitations to any one or more of the physical dimensions of the system, as the dimensions of the system may depend, at least in part, on the article to be secured, the tissue to which it may be secured, and the securing device. In some non-limiting embodiments, the exterior tube 31 may have a diameter of about 3 mm to about 8 mm. Examples of the diameter of the exterior tube 31 may include a diameter of about 3 mm, about 4 mm, about 5 mm, about 6 mm, about 7 mm, about 8 mm, and any value or range between any two of these values including endpoints. In one non-limiting example, the exterior tube 31 may have a diameter of about 5 mm.

The system may also include a medial tube 34 disposed at least partially within the exterior tube 31, an interior tube 36 at least partially disposed within the medial tube, and a push rod 38 at least partially disposed within the interior tube.

The medial tube 34 may be composed of one or more of a metal and a plastic. In some non-limiting examples, the medial tube 34 may be composed of one or more of a stainless steel, a nickel titanium alloy, and a cobalt chrome alloy. In some other non-limiting examples, the medial tube 34 may be composed of or more of a polyether ether ketone, a polyether block amide, a polytetrafluoroethylene, a fluorinated ethylene propylene, and an extended polytetrafluoroethylene.

The interior tube 36 may be composed of one or more of a metal and a plastic. In some non-limiting examples, the medial tube 36 may be composed of one or more of a stainless steel, a nickel titanium alloy, and a cobalt chrome alloy. In some other non-limiting examples, the medial tube 36 may be composed of or more of a polyether ether ketone, a polyether block amide, a polytetrafluoroethylene, a fluorinated ethylene propylene, and an extended polytetrafluoroethylene.

The push rod 38 may be composed of a metal. In some non-limiting examples, the push rod 38 may be composed of one or more of a stainless steel, a nickel titanium alloy, and a cobalt chrome alloy.

As depicted in FIG. 3A, the interior tube 36 may have an exterior surface, the medial tube 34 may have an interior surface, and the interior tube and the medial tube may be configured to releasably engage the at least one securing device 10 in the first deployment state therebetween. The medial tube 34 may have a distal end configured to engage a slot between a tab and the body of the securing device 10. Additionally, the push rod 38 may have a distal end configured to engage an end of the tab of the securing device 10. In one non-limiting embodiment, the interior tube 36 may further have at least one detent configured to form a mechanical contact with at least one friction protrusion of the at least one securing device 10.

The securing device and system depicted in FIGS. 3A-3C may operate in the following manner. As illustrated in FIG. 3A, a securing device 10 having a linearly extended deployment state may be engaged by the system in a space between the medial tube 34 and the interior tube 36. A distal end of the interior tube 36 may engage a slot of the securing device 10 and the exterior end of the push rod 38 may engage a tip end of the tab of the securing device. The article 2 may be stabilized against the surface of the tissue 3 by the pawl 32. As illustrated in FIG. 3B, the push rod 38 and interior tube 36 may be moved in a distal direction. Because of the engagement of the slot with the interior tube 36 and the tab with the push rod 38, the securing device 10 may be displaced in the distal direction, thereby forcing the first portion of the securing device to penetrate the tissue 3 and releasing the securing device 10 from the system. The first portion of the securing device 10 may continue penetrating the tissue 3 until the tab standoff 37 contacts the surface of the tissue. The first portion of the securing device 10, free of the system, may then assume a curved geometry within the tissue 3, constituting a portion of the securing state of the device. As illustrated in FIG. 3C, once the first portion of the securing device 10 has assumed a curved geometry within the tissue 3, thereby anchoring at least a portion of the securing device, the medial tube 34 and the interior tube 36 may be moved in the proximal direction. In this manner, the second portion of the securing device 10 may be freed from the system and allowed to assume the curved geometry of the securing state. In some embodiments, the securing state may include the second portion of the securing device 10 forming a curved contact with at least a portion of the surface of the article 2.

Figure 4A:
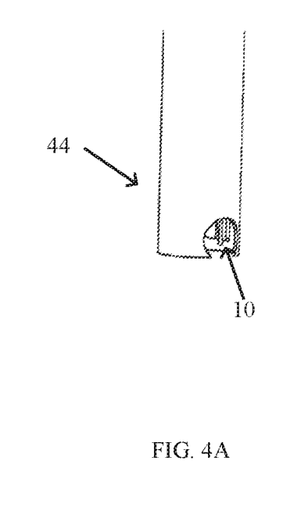
FIGS. 4A-4D depict use of a system to secure an article to a surface of a tissue using a securing device having a U-shaped deployment state according to an embodiment.
Figure 4B:
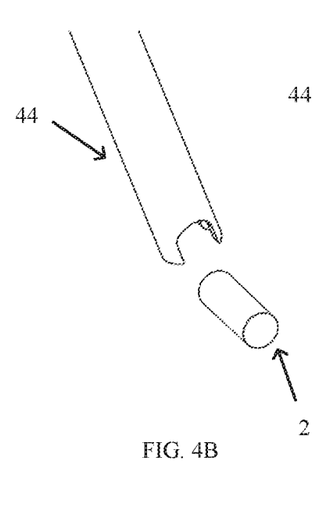
Figures 4C, 4D:
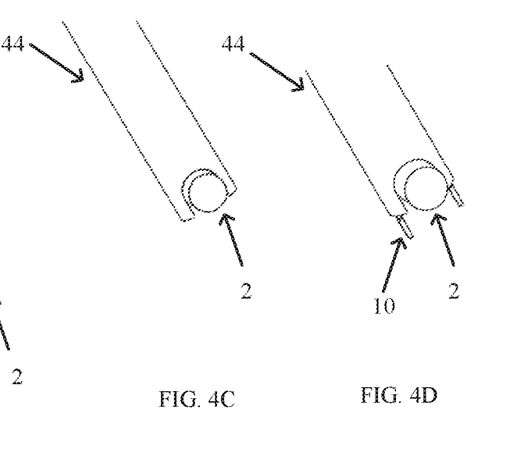

An alternative embodiment of a system for securing an article to a tissue is depicted in FIGS. 4A-4D. In the system depicted in FIGS. 4A-4D, the securing device may be one having a U-shaped deployment state. In FIG. 4A, the one or more securing devices 10 may initially be engaged within the delivery system 44. The delivery system 44 may include a distal end having a surface geometry complementary to the geometry of at least a portion of an external surface of the article to be secured. As depicted in FIG. 4B, the delivery system 44 may be brought in proximal contact to the article 2 to be secured. The article 2 may be contacted with the distal end of the system 44 at the distal end having the complementary geometry to the article, as depicted in FIG. 4C. FIG. 4D illustrates that a securing device 10 may be released from the system 44 to contact the article 2. The securing device 10 may be released from the system 44 according to any of a number of means including the use of a push rod (not shown).

Figure 5A:
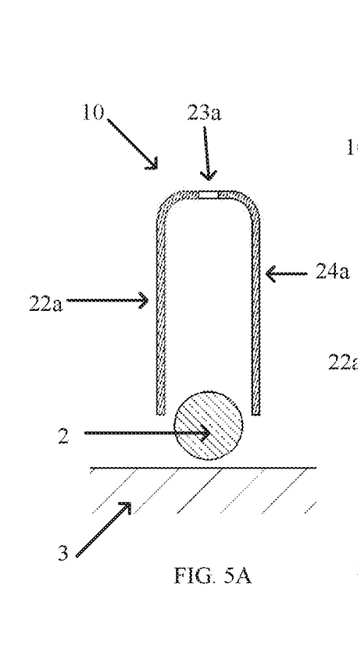
FIGS. 5A-5D depict a manner in which an article may be secured to a surface of a tissue by the use of a securing device having a U-shaped deployment state according to an embodiment.
Figures 5B, 5C:
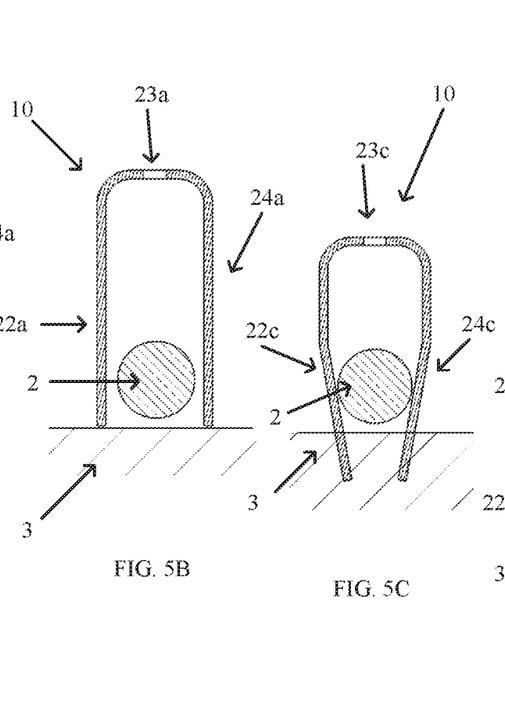
Figure 5D:
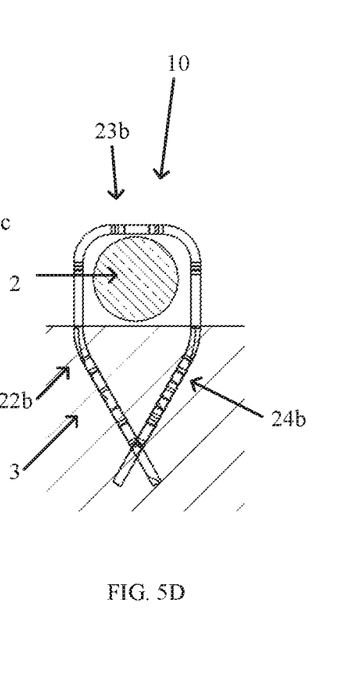

FIGS. 5A-5D depict the interaction of a securing device 10 with an article 2 and a tissue 3 to which the article may be secured. As illustrated in FIGS. 5A-5D, the securing device 10 may be one having a U-shaped deployment state. FIG. 5A illustrates the article 2 proximate to the surface of the tissue 3. The securing device 10 may be in a deployment state, as indicated by the U-shape of the securing device. In the deployment state, such a securing device 10 may have a first portion 22a, and a second portion 24a in a roughly parallel orientation. A medial portion 23a is disposed between the first portion 22a and the second portion 24a. Together, the first portion 22a, the second portion 24a, and the medial portion 23a may surround the article 2. As depicted in FIG. 5B, the first terminal end from the first portion 22a, and the second terminal end of the second portion 24a may contact the surface of the tissue 3. As illustrated in FIG. 5B, the securing device 10 may still be in the deployment state, as indicated by the index letter 'a' associated with each of the figure component labels. The securing device 10, as illustrated in FIG. 5C, may be advanced in a distal direction, causing the first section 22c and the second section 24c to begin their respective transitions from the deployment state to the securing state (as indicated by the letter 'c' in the component labels.) The medial portion 23c may also transition between a deployment state to a securing state. In FIG. 5D, the securing device 10 has transitioned to the securing state, as indicated by the index letter 'b' associated with each of the figure component labels. In the securing state, the first portion 22b and second portion 24b may assume their respective curved geometries within the tissue 3. The article 2 may thus be anchored to the surface of the tissue 3 by means of the first portion 22b, second portion 24b, and medial portion 23b of the securing device 10.

Figure 6:
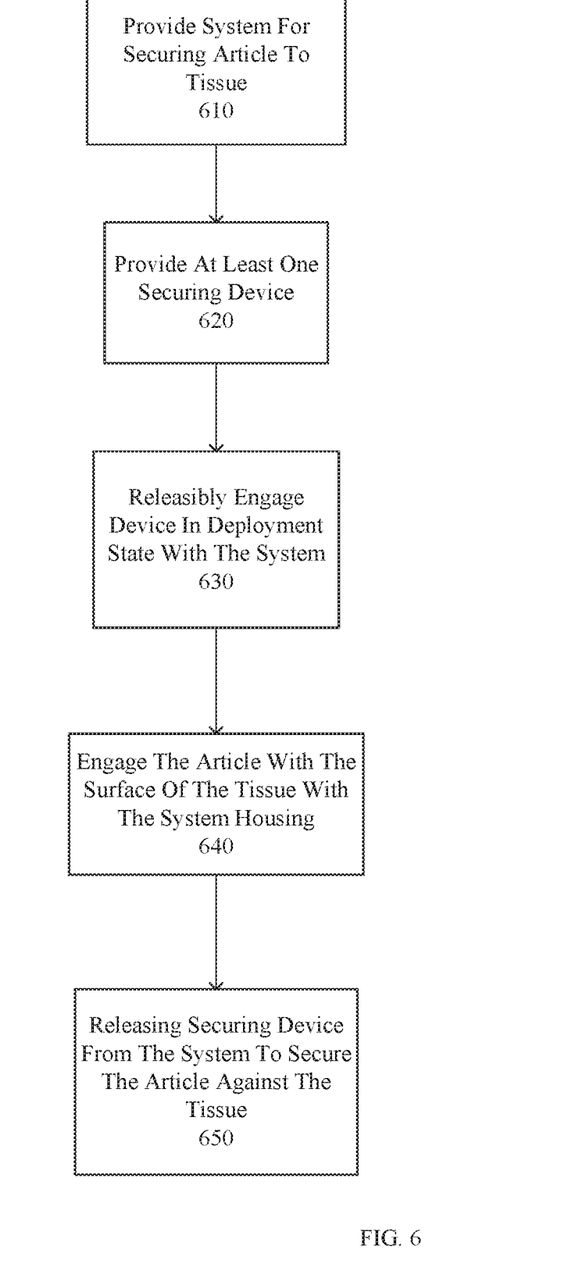
FIG. 6 is a flow chart for a method of securing an article to a surface of a tissue using a securing device having a deployment state and a securing state according to an embodiment.

FIG. 6 is a flow chart of a method for securing an article to a tissue. The method may include providing 610 a system for securing the article to the tissue. In some embodiments, the system may include a housing having a distal end, in which at least a portion of the distal end of the housing may be configured to engage the article with a surface of the tissue. In some non-limiting examples, the system for securing the article to the tissue may further include a medial tube at least partially disposed within the system housing, an interior tube at least partially disposed within the medial tube, and a push rod at least partially disposed within the interior tube.

The method may also include providing 620 at least one securing device. In some embodiments, the at least one securing device may include a body, transitionable from a first deployment state to a second securing state, having a first portion, a second portion, and a medial portion between the first portion and the second portion. The first portion of the securing device may further have a first terminal end configured to pierce the tissue. Additionally, the second securing state of the securing device may include at least a section of the first portion of the body assuming a curved geometry embedded in the tissue and at least a section of the medial portion of the body contacting a surface of the article.

In one non-limiting example, the first deployment state of the securing device may take the form of a U-shaped state, and the second securing state may include at least a section of a first terminal end of the first portion assuming a curved geometry embedded in the tissue, at least a section of a second terminal end of the second portion assuming a curved geometry embedded in the tissue, and at least a section of the medial portion contacting a surface of the article In another non-limiting example, the first deployment state of the securing device may take the form of a linearly extended state, and the second securing state may further include at least a section of the first portion of the body assuming a curved geometry embedded in the tissue and at least a section of the second portion contacting a surface of the article. In some additional non-limiting examples, the securing device may further include a tab standoff in mechanical communication with the medial portion of the body at a first standoff end and a tab at a second standoff end, in which the tab may be displaced by a slot from the body.

The securing device, while in a deployment state, may be releasibly engaged 630 with the deployment system. In some embodiments, the at least one securing device may include a tab standoff in mechanical communication with the medial portion of the body of the securing device at a first standoff end and a tab at a second standoff end, thereby displacing the tab from the body by a slot. For such a securing device, releasibly engaging 630 the device within the system for securing the article may further include releasibly engaging the slot of the device with a portion of the deployment system. In one example, such a deployment system may include an interior tube having a distal end that may engage 630 the slot of the securing device.

In some embodiments, the at least one securing device may also include a friction protrusion in mechanical communication with the body and proximate to a tab. For such a securing device, releasibly engaging the device within the system for securing the article may further include releasibly engaging the friction protrusion with a detent on an exterior surface of an interior tube of the deployment system.

The deployment system may be used to engage 640 the article with the surface of the tissue. In some embodiments, the article may be engaged 640 with the surface of the tissue using at least a portion of a distal end of the housing.

The securing device may be released 650 from the deployment system, thereby allowing the body of the securing device to assume the second securing state and securing the article against the surface of the tissue. In some non-limiting embodiments, releasing 650 the securing device from the distal end of the housing may include contacting the tab of the securing device with a distal end of a deployment system push rod, extending the push rod in a distal direction, and extending a medial tube of the deployment system in a proximal direction.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera As a non-limiting example, each range discussed herein can be readily broken down into a lower third, middle third and upper third, et cetera As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A system for securing an article to a tissue by releasably engaging at least one securing device, the system comprising:
    a tube comprising a distal end configured to contact the tissue;
    a push rod at least partially disposed within the tube; and
    a securing device at least partially disposed within the tube, the securing device comprising a first portion, a second portion, and a medial portion disposed between the first portion and the second portion, wherein the first portion and the second portion are each transitionable from a first deployment state to a second securing state; and
    a tab standoff comprising a first end coupled to the medial portion of the securing device, a tab at a second end, and a slot disposed between the tab and the medial portion of the securing device,
    wherein the push rod is engagable with the tab standoff.

2. The system of claim 1, wherein a distal end of the push rod is engageable with the tab of the tab standoff.

3. The system of claim 1, wherein the system comprises a plurality of securing devices each with a tab standoff coupled to the medial portion of the securing device.

4. The system of claim 1, further comprising an interior tube that is at least partially disposed within the tube and the push rod is at least partially disposed within the interior tube.

5. The system of claim 4, wherein a distal end of the interior tube is engagable with the slot between the tab and the medial portion of the securing device.

6. The system of claim 4 wherein the interior tube is movable relative to the exterior tube.

7. The system of claim 6, wherein the interior tube is configured to release the second portion of the securing device when withdrawn proximally into the tube, thereby causing the second portion of the securing device to transition from the first deployment state to the second securing state.

8. The system of claim 4, further comprising a medial tube is at least partially disposed within the tube,
   wherein the interior tube is at least partially disposed within the medial tube.

9. The system of claim 8, wherein the securing device and the tab standoff are at least partially disposed within the medial tube.

10. The system of claim 9, wherein a distal end of the medial tube is configured to contact the tissue.

11. The system of claim 1, wherein the securing device further comprises a friction protrusion that projects from the medial portion.

12. The system of claim 11, wherein the friction protrusion is proximate to the tab of the tab standoff.

13. The system of claim 11, wherein the tab of the tab standoff is opposite the friction protrusion without making physical contact with each other.

14. The system of claim 11, wherein the tab is in mechanical contact with the friction protrusion.

15. The system of claim 1, wherein the second portion of the securing device has a terminal end comprising a blunt tip.

16. The system of claim 1, wherein the tube comprises a pawl having a surface geometry complementary to a geometry of at least a portion of an external surface of the article.

* * * * *